United States Patent [19]

Kawai et al.

[11] Patent Number: 4,620,042
[45] Date of Patent: Oct. 28, 1986

[54] PREPARATION OF 2-CHLORO-4-FLUOROPHENOL FROM 4-FLUOROPHENOL

[75] Inventors: Toshikazu Kawai, Kawagoe; Ysunobu Nishimura; Katumi Kanesaki, both of Kamifukuoka, all of Japan

[73] Assignee: Central Glass Company, Limited, Ube, Japan

[21] Appl. No.: 709,435

[22] Filed: Mar. 7, 1985

[30] Foreign Application Priority Data

Mar. 13, 1984 [JP] Japan ................... 59-46607

[51] Int. Cl.$^4$ ............................. C07C 39/27
[52] U.S. Cl. ................... 568/775; 568/774; 568/779
[58] Field of Search ............ 568/774, 775, 779

[56] References Cited

U.S. PATENT DOCUMENTS

| | | | |
|---|---|---|---|
| 1,847,566 | 3/1932 | Laschinger | 568/779 |
| 2,659,759 | 11/1953 | Zemba | 568/779 |
| 2,759,981 | 8/1956 | Pray et al. | 568/779 |
| 3,318,949 | 5/1967 | Roberts et al. | 568/779 |
| 4,489,210 | 12/1984 | Judat et al. | 568/779 |

FOREIGN PATENT DOCUMENTS

| | | | |
|---|---|---|---|
| 0025344 | 2/1984 | Japan | 568/775 |
| 926014 | 5/1963 | United Kingdom | 568/779 |
| 2135310 | 8/1984 | United Kingdom | 568/776 |
| 154249 | 9/1963 | U.S.S.R. | 568/775 |
| 201360 | 2/1968 | U.S.S.R. | 568/779 |
| 252319 | 10/1975 | U.S.S.R. | 568/779 |

OTHER PUBLICATIONS

Groves, et al, The Scission of Diaryl Ethers and Related Compounds by Means of Piperidine, Part II., The Nitration of 2:4:4'-Trichlorodiphenyl Ether, and of 2:4 Dichlorophenyl p-Toluenesulphonate and Benzoate, Journal of the Chemical Society, London, 1929, p. 516.
J. Am. Chem. Soc., 81,94–101, (1959).
U.S.S.R. Pat. No. 154,250, (Chem. Abstr., 2835 (1963)).
Zhurnal Obshchei Khimii, 27, 2486-87 (1967) (Chem. Abstr., vol. 68, 114200z (1968)).

*Primary Examiner*—Werren B. Lone
*Attorney, Agent, or Firm*—Fleit, Jacobson, Cohn & Price

[57] ABSTRACT

2-Chloro-4-fluorophenol is obtained with good yield by direct chlorination of 4-fluorophenol with chlorine gas at 0°–185° C. in the absence of catalyst. In a combination of these reactants, the selectivity to the substitution chlorination reaction at the 2-position of 4-fluorophenol is uncommonly high and reaches about 99% under optimum conditions. 4-Fluorophenol is subjected to the reaction as either pure liquid or solution in a suitable organic solvent such as carbon tetrachloride or acetic acid.

6 Claims, No Drawings

PREPARATION OF 2-CHLORO-4-FLUOROPHENOL FROM 4-FLUOROPHENOL

BACKGROUND OF THE INVENTION

This invention relates to a method of preparing 2-chloro-4-fluorophenol by direct chlorination of 4-fluorophenol.

2-Chloro-4-fluorophenol is useful as an intermediate material for medicines and agricultural chemicals since some derivatives of this compound exhibit remarkable physiological activities as represented by its 4-phenylurazole derivative.

Heretofore it has been believed to be difficult to substitute chlorine for hydrogen in the ring of 4-fluorophenol preferentially and exclusively at the 2-position. Accordingly, rather complicated substitution methods have been proposed for the preparation of 2-chloro-4-fluorophenol. According to J. Am. Chem. Soc., 81, 94 (1959), this compound is obtained through the steps of nitrating 4-fluoroanisole, aminating the nitro group by reduction, substituting the amino group by chlorine atom by the Sandmeyer reaction, and finally cleaving the ether bond. Though selective substitution at the 2-position is ensured, this method is not suited to industrial practice because of being a very roundabout process comprising various kinds of reactions. U.S.S.R. Pat. No. 154,250 proposes to obtain 2-chloro-4-fluorophenol by first chlorinating an alkali metal salt of 4-fluorophenol at its 2-position by using an alkali metal hypochlorite as the chlorinating agent. However, this method needs a complementary procedure to convert the chlorinated fluorophenolate into 2-chloro-4-fluorophenol, and the operations are troublesome.

To achieve direct chlorination of 4-fluorophenol at its 2-position, Zh. Obshch. Khim., 37, 2486(1967) shows the use of sodium hypochlorite or sulfuryl chloride as a chlorinating agent that is high in selectivity to the substitution at the 2-position. However, this simplified chlorination method cannot be regarded as an industrially profitable method because the yield of 2-chloro-4-fluorophenol based on 4-fluorophenol remains at a level of 82–92%.

SUMMARY OF THE INVENTION

It is an object of the present invention to provide an industrially favorable method of preparing 2-chloro-4-fluorophenol from 4-fluorophenol.

A method according to the invention for the preparation of 2-chloro-4-fluorophenol is characterized by comprising the step of making react chlorine gas with 4-fluorophenol at a temperature in the range from about 0° C. to about 180° C. in the absence of catalyst.

As a chlorinating agent, chlorine gas is known as to be very high in the chlorinating power and low in the selectivity to substitution chlorination at a specific position of benzene ring. However, we have discovered an unexpected fact that in the case of reacting with 4-fluorophenol chlorine gas exhibits very high selectivity to the substitution chlorination at the 2-position. This tendency is very unique and does not apply to the chlorination of resembling compounds. For example, our trial of chlorination of 4-fluoroanisole, which is a derivative of 4-fluorophenol, by chlorine gas with the intention of obtaining 2-chloro-4-fluorophenol by cleavage of the ether bond of the clorinated anisole revealed that the selectivity to the chlorination reaction at the 2-position is too low from an industrial point of view.

In the method of the invention, no catalyst is used for the chlorination reaction. If the reaction is carried out in the presence of a popular chlorination catalyst such as ferric chloride or cupric oxide, the metal ions of the catalyst adversely affect the selectivity to the reaction at the 2-position of 4-fluorophenol.

In this method, 4-fluorophenol is used in a liquid form by the aid of either heat or a suitable solvent.

The present invention has made it possible to convert 4-fluorophenol into 2-chloro-4-fluorophenol very easily and very efficiently and can readily be put into industrial practice with a fair profit. The starting material, 4-fluorophenol can be obtained by a known process such as alkaline hydrolysis of 4-bromofluorobenzene under superatmospheric pressure conditions.

DESCRIPTION OF THE PREFERRED EMBODIMENTS

As mentioned above, the reaction according to the invention is carried out by making chlorine gas contact with 4-fluorophenol in a liquid form. One way of keeping 4-fluorophenol in liquid form is to maintain its temperature above the melting point and below the boiling point. Another way is to dissolve 4-fluorophenol in a suitable organic solvent which does not react with the phenol and neither with chlorine gas, such as carbon tetrachloride, trichloromethane or acetic acid. The range of the reaction temperature is specified to be from about 0° C. to about 185° C. with consideration of the cases of using a solution of 4-fluorophenol too. In choosing a solvent, care should be taken not to lower the selectivity to substitution chlorination at the 2-position of 4-fluorophenol by the influence of the solvent itself or some impurities possibly contained in the solvent. In the same sense, the material of the reaction vessel should be selected so that any obstructive substance, and particularly metal ions such as iron ions, cobalt ions or copper ions, may not dissolve into the reaction liquid from the vessel material.

Usually the chlorination reaction is carried out by introducing chlorine gas at an appropriate feed rate into 4-fluorophenol initially charged in a reaction vessel. The mole ratio of total chlorine gas to 4-fluorophenol is not critical. However, it is undesirable to use a large excess of chlorine gas from the viewpoint of preventing the formation of highly chlorinated by-products such as 2,6-dichloro-4-fluorophenol and 2,5,6-trichloro-4-fluorophenol. Therefore, it is suitable to use approximately 1 mole of chlorine gas per mole of 4-fluorophenol. The yield of 2-chloro-4-fluorophenol based on 4-fluorophenol is nearly proportional to the amount of the feed of chlorine gas. For example, when 0.5 mole of chlorine gas is supplied per mole of 4-fluorophenol the yield of 2-chloro-4-fluorophenol is about 0.5 mole per mole of the starting material.

The invention will further be illustrated by the following nonlimitative examples.

EXAMPLE 1

Initially, 10 g of 4-fluorophenol was charged in a reaction vessel which was made of glass and was provided with a chlorine gas feed pipe. The starting material was kept heated at about 55° C., and chlorine gas was bubbled into the starting material at such a rate that in 30 min the total quantity of the supplied chlorine gas reached equivalent to the initial quantity of 4-fluorophenol by mole. During this operation, hydrogen chloride gas evolved by the reaction was continuously discharged from the reaction system through an efficient reflux condenser connected to the reaction vessel.

After completion of the chlorination operation, the liquid in the reactor was found to be a mixture of 98.4% of 2-chloro-4-fluorophenol, 1.4% of more highly chlorinated by-products and 0.2% of unreacted 4-fluorophenol, by mole. Therefore, selectivity of chlorination to 2-chloro-4-fluorophenol was 98.6%, and the yield of this compound based on 4-fluorophenol was 98.4%.

EXAMPLE 2

The chlorination process of Example 1 was repeated under the same conditions except that the reaction temperature was raised to 150° C.

After completion of the chlorination operation, the reaction liquid consisted of 97.3% of 2-chloro-4-fluorophenol, 2.5% of more highly chlorinated by-products and 0.2% of unreacted 4-fluorophenol, by mole. Therefore, selectivity of chlorination to 2-chloro-4-fluorophenol was 97.5% and the yield of this compound based on 4-fluorophenol was 97.3%.

EXAMPLE 3

Using the apparatus described in Example 1, 44 g of 4-fluorophenol was chlorinated by the same method as in Example 1 except that the reaction was carried out at 90° C. and that the feed of 1 mole of chlorine gas per mole of 4-fluorophenol took 60 min.

After completion of the chlorination operation, the reaction liquid consisted of 98.9% of 2-chloro-4-fluorophenol, 1.0% of more highly chlorinated by-products and 0.1% of unreacted 4-fluorophenol, by mole. Therefore, selectively of chlorination to 2-chloro-4-fluorophenol was 99.0% and the yield of this compound based on 4-fluorophenol was 98.9%.

EXAMPLE 4

A solution of 12 g of 4-fluorophenol in 6 g of carbon tetrachloride was charged in the glass vessel used in Example 1. Maintaining the temperature of the solution at about 30° C., chlorine gas was bubbled into the solution at such a rate that in 30 min the total quantity of the supplied chlorine gas reached equivalent to the initial quantity of 4-fluorophenol by mole. During this operation, hydrogen chloride gas evolved by the reaction was continuously discharged from the reaction system in the same manner as in Example 1.

After completion of the chlorination operation, carbon tetrachloride used as solvent was completely removed by distillation to leave a reaction liquid, which consisted of 95.4% of 2-chloro-4-fluorophenol, 3.6% of more highly chlorinated by-products and 1.1% of unreacted 4-fluorophenol, by mole. Therefore, selectivity of chlorination to 2-chloro-4-fluorophenol was 96.3% and the yield of this compound based on 4-fluorophenol was 95.4%.

REFERENCE

In this case, 10 g of 4-fluoroanisole was charged in the glass vessel used in Example 1 and was kept heated at about 50° C. Chlorine gas was bubbled into the starting material at such a rate that in 30 min the total quantity of the supplied chlorine gas reached equivalent to the initial quantity of 4-fluoroanisole by mole. During this operation, hydrogen chloride gas evolved by the reaction was continuously discharged in the same manner as in Example 1.

After completion of the chlorination operation, the liquid in the reaction vessel was a mixture of 76.9% of 2-chloro-4-fluoroanisole, 18.3% of more highly chlorinated by-products and 4.8% of unreacted 4-fluoroanisole, by mole. Therefore, selectivity of chlorination to 2-chloro-4-fluoroanisole was 80.8% and the yield of this compound based on 4-fluoroanisole was 76.9%. This liquid mixture was subjected to reflux together with hydrobromic acid for 20 hr to thereby cleave the ether bond of the anisole. It was confirmed that most of 2-chloro-4-fluoroanisole in the mixture was converted into 2-chloro-4-fluorophenol. Through this operation the selectivity to 2-chloro-4-fluorophenol was calculated to be 75.2%, and the yield of this compound based on 4-fluoroanisole was only 60.0%.

What is claimed is:

1. A method of preparing 2-chloro-4-fluorophenol, comprising the step of making react chlorine gas with 4-fluorophenol at a temperature in the range from about 0° C. to about 185° C. in the absence of catalyst and substantially in the absence of metal ions.

2. A method according to claim 1, wherein 4-fluorophenol is subjected to the reaction in its liquid state.

3. A method according to claim 1, further comprising the step of dissolving 4-fluorophenol in a substantially unreactive organic solvent before the reaction with chlorine gas.

4. A method according to claim 3, wherein said solvent is selected from the group consisting of carbon tetrachloride, trichloromethane and acetic acid.

5. A method according to claim 1, wherein the reaction is carried out by initially charging 4-fluorophenol in a reaction vessel and then gradually introducing chlorine gas into the reaction vessel until the total quantity of the introduced chlorine gas becomes approximately equivalent by mole to the initial quantity of 4-fluorophenol in the reaction vessel.

6. A method according to claim 5, further comprising the step of discharging hydrogen chloride gas evolved by the reaction from the reaction vessel while chlorine gas is reacting with 4-fluorophenol.

* * * * *